(12) United States Patent
Tegzes et al.

(10) Patent No.: US 12,708,449 B2
(45) Date of Patent: Aug. 18, 2026

(54) ARTIFICIAL INTELLIGENCE SYSTEM AND METHOD FOR DEFINING AND VISUALIZING PLACEMENT OF A CATHETER IN A PATIENT COORDINATE SYSTEM TOGETHER WITH AN ASSESSMENT OF TYPICAL COMPLICATIONS

(71) Applicant: GE Precision Healthcare LLC, Wauwatosa, WI (US)

(72) Inventors: Pál Tegzes, Budapest (HU); Zita Herczeg, Szeged (HU); Hongxu Yang, Utrecht (NL); Zoltán Kiss, Budapest (HU); Balázs P. Cziria, Budapest (HU); Poonam Dalal, Brookfield, WI (US); Alec Baenen, Hartland, WI (US); Gireesha Rao, Pewaukee, WI (US); Beth Heckel, Waukesha, WI (US); Pulak Goswami, Nashville, TN (US); Dennis Zhou, Jamesville, NY (US); Gopal Avinash, Concord, CA (US); Lehel Ferenczi, Budapest (HU); Katelyn Nye, Glendale, WI (US); Noah Thompson Orfield, Nashville, TN (US); Emma Neal, Nashville, TN (US); Sarah Ouadah, Nashville, TN (US)

(73) Assignee: GE Precision Healthcare LLC, Waukesha, WI (US)

( * ) Notice: Subject to any disclaimer, the term of this patent is extended or adjusted under 35 U.S.C. 154(b) by 301 days.

(21) Appl. No.: 18/385,448

(22) Filed: Oct. 31, 2023

(65) Prior Publication Data

US 2024/0164845 A1 May 23, 2024

Related U.S. Application Data

(60) Provisional application No. 63/427,646, filed on Nov. 23, 2022.

(51) Int. Cl.
*A61B 34/20* (2016.01)
*A61B 6/00* (2006.01)
(Continued)

(52) U.S. Cl.
CPC ................ *A61B 34/20* (2016.02); *A61B 6/12* (2013.01); *A61B 6/463* (2013.01); *A61B 6/54* (2013.01);
(Continued)

(58) Field of Classification Search
CPC ........... A61B 34/20; A61B 6/12; A61B 6/463; A61B 6/54; A61B 2034/2065;
(Continued)

(56) References Cited

U.S. PATENT DOCUMENTS 11,410,341 B2 8/2022 Baenen et al.
2018/0240237 A1* 8/2018 Donhowe ............. G06T 7/0014
(Continued)

FOREIGN PATENT DOCUMENTS

WO 2020226693 A1 11/2020

OTHER PUBLICATIONS

Baskin et al., Cavoatrial Junction and Central Venous Anatomy: Implications for Central Venous Access Tip Position, Journal of Vascular Interventional Radiology 2008; 19:359-365.
(Continued)

*Primary Examiner* — Neil R Mclean
(74) *Attorney, Agent, or Firm* — Boyle Fredrickson, S.C.

(57) ABSTRACT

An image processing system and method is provided. The image processing system includes a display, a processor, and a memory. The memory stores processor-executable code that when executed by the processor causes receiving an image of a region of interest of a patient with a medical catheter, tube or line disposed within the region of interest, detecting the medical tube or line within the image, gener-
(Continued)

ating a patient coordinate system relative to an anatomy of the patient within the image, generating a combined image by superimposing a first graphical marker on the image that indicates an end of the medical catheter, tube or line, and a second graphical marker on the image that indicates patient coordinate system, and displaying the combined image on the display. In addition, the system assesses common visualizable complications associated with CVC placement, including but not limited to hydrothorax, pneumothorax, pneumomediastinum and CVC position changes between x-rays taken at different times.

20 Claims, 8 Drawing Sheets

(51) Int. Cl.
*A61B 6/12* (2006.01)
*A61B 6/46* (2024.01)
*G06T 7/73* (2017.01)
*G06T 11/00* (2006.01)

(52) U.S. Cl.
CPC ................ *G06T 7/74* (2017.01); *G06T 11/00* (2013.01); *A61B 2034/2065* (2016.02); *G06T 2207/30012* (2013.01); *G06T 2207/30204* (2013.01); *G06T 2210/41* (2013.01)

(58) Field of Classification Search
CPC ....... A61B 6/5217; A61B 6/4405; G06T 7/74; G06T 11/00; G06T 2207/30012; G06T 2207/30204; G06T 2210/41; G06T 2207/10116; G06T 2207/30101; G06T 7/337
USPC .......................................................... 382/128
See application file for complete search history.

(56) References Cited

U.S. PATENT DOCUMENTS

| | | | | |
|---|---|---|---|---|
| 2021/0224984 | A1* | 7/2021 | Holsing ............. | A61B 10/0283 |
| 2022/0133284 | A1 | 5/2022 | Lampotang | |
| 2023/0363832 | A1* | 11/2023 | Mosadegh ............. | G16H 20/40 |

OTHER PUBLICATIONS

Vannucci et al., Retained Guidewires After Intraoperative Placement of Central Venous Catheters, Anesthesia Patient Safety Foundation, Jul. 2013, pp. 102-108, vol. 117, No. 1.
Kombau et al., Central line complications, International Journal of Critical Illness & Injury Science, Jul.-Sep. 2015.
Jung et al., Classification of Central Venous Catheter Tip Position on Chest X-ray Using Artificial Intelligence, Journal of Personalized Medicine, 2022.
EP application 23209903.6 filed Nov. 14, 2023—Search report issued Apr. 2, 2024; 8 pages.

* cited by examiner

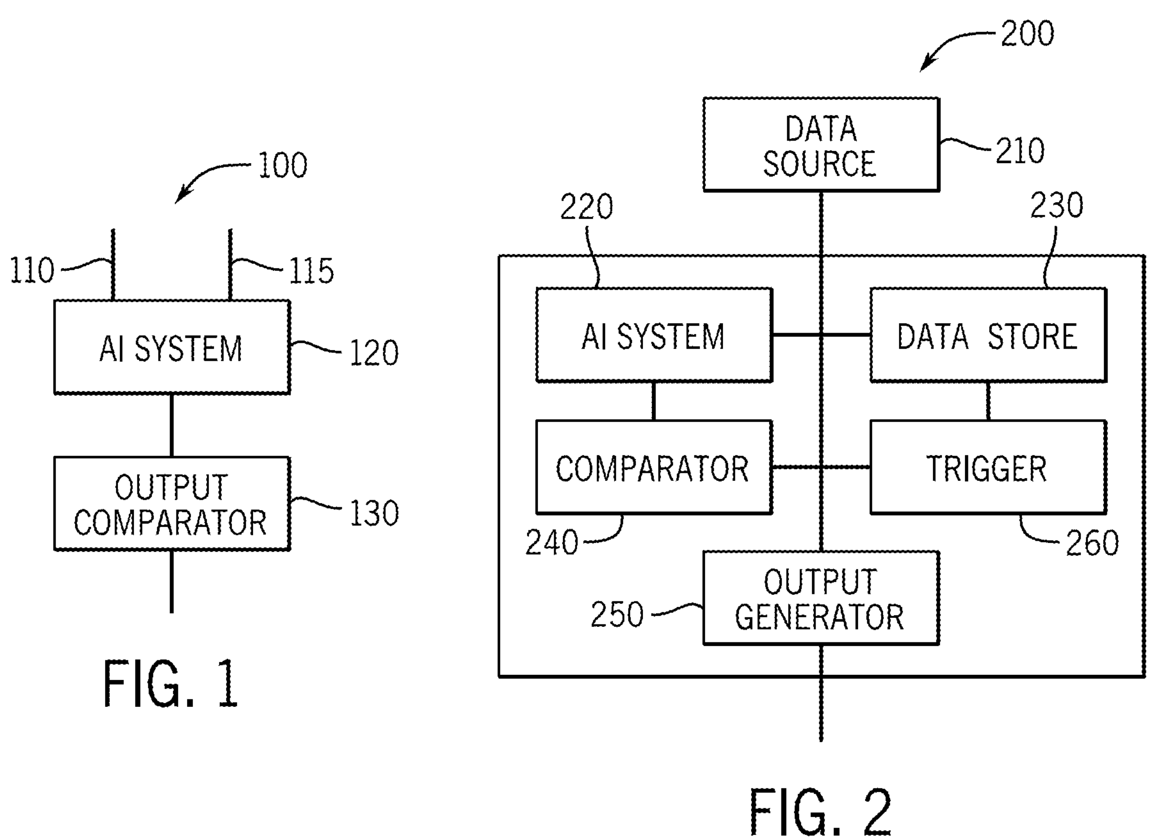
FIG. 1
FIG. 2
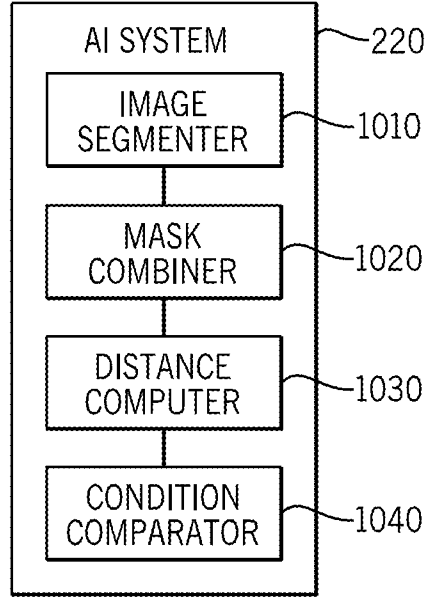
FIG. 3

ARTIFICIAL INTELLIGENCE SYSTEM AND METHOD FOR DEFINING AND VISUALIZING PLACEMENT OF A CATHETER IN A PATIENT COORDINATE SYSTEM TOGETHER WITH AN ASSESSMENT OF TYPICAL COMPLICATIONS

CROSS-REFERENCE TO RELATED APPLICATIONS

This application claims priority from U.S. Provisional Patent Application Ser. No. 63/427,646, filed on Nov. 23, 2022, the entirety of which is expressly incorporated by reference herein for all purposes.

FIELD OF THE DISCLOSURE

The subject matter disclosed herein relates to medical image processing, and more particularly to systems and methods for visualizing placement of a medical tube or line.

BACKGROUND OF THE DISCLOSURE

Medical imaging may be utilized to visualize medically placed tubes or lines (e.g., a chest tube, a nasogastric tube, a endotracheal tube, a vascular line, a peripherally inserted central catheter (PICC), a catheter, etc.). However, it may be difficult for medical personnel (e.g., the doctor, radiologist, technician, etc.) to visualize these medically placed tubes or lines. In addition, the medical personnel may be untrained or inexperienced, which may hinder their ability to identify the medically placed tube or line and to determine if it is properly placed. Further, medical personnel may have to manually assess typical complications associated with the tube/line placement and make measurements (which may be time consuming) to determine if a medically placed tube or line is properly placed. However, if a medically placed tube or line is misplaced, fast intervention is needed to move the tube or line to the appropriate location for patient safety.

In order to assist with the visualization and placement of the tube(s) within the patient, certain systems and methods have been developed, such as that disclosed in U.S. Pat. No. 11,410,341 (the '341 Patent), entitled System And Method For Visualizing Placement Of A Medical Tube Or Line, the entirety of which is expressly incorporated herein by reference for all purposes. In the '341 patent, an artificial intelligence (AI) is trained to be employed as part of an image processing system including a display, a processor, and a memory. The memory stores processor-executable code for the trained AI that when executed by the processor causes receiving an image of a region of interest of a patient with a medical tube, e.g., an endotracheal tube (ETT) or nasogastric tube (NGT), or peripherally inserted central catheter (PICC) line, disposed within the region of interest, detecting the medical tube or line within the image, generating a combined image by superimposing a first graphical marker on the image that indicates an end of the medical tube or line as well as a reference point of the patient anatomy, and displaying the combined image on the display.

While the above-mentioned devices fulfill important medical purposes, their placement or misplacement may also have some adverse side effects or complications. So when such devices are present in an image, the users may want to verify whether the typical complications associated with the given devices are present or not. For example, if the presence of one or more central venous access catheter/pulmonary artery catheter (CVC/PAC) devices are detected in an image, then it's useful to check the image for the presence of their typical complications: including but not limited to retained guide wires, pneumothoraxes, hydrothoraxes, hemothoraxes, pneumomediastinums, and pericardial effusions.

As a result, while the determination of the tube or line tip and the reference point provides the user with sufficient information to determine if the point of the tube or line is in the proper location, for the proper placement of a CVC/PAC it is also desirable to illustrate the course of the CVC/PAC to the tip, as well as to provide information regarding the presence of any complications that the placement of the devices might have induced.

In addition, the assessment of the proper location of the CVC/PAC may be influenced by the positioning and/or size of the patient. More specifically, the patient may be rotated with respect to the primary axes and/or plane of the image, and therefore the measurement of a vertical distance between points of interest should most preferably be made in a direction adapted to the position of the patient. In addition, the optimal distance and/or position of the CVC/PAC may depend on the patient size, such that a distance that is optimal for a large adult may be too long for a small or pediatric patient. To account for these differences in the sizes of the individual patients, the distance may be measured in units adapted to the particular patient size. For example, the distance between the carina and the CVC/PAC tip may be measured in vertebral body units as proposed in Baskin et al., *Cavoatrial Junction and Central Venous Anatomy: Implications for Central Venous Access Tip Position*, Journal of Vascular Interventional Radiology 2008; 19:359-365, which is incorporated herein by reference in its entirety for all purposes.

Therefore, to enable a physician/user to more readily achieve the proper placement of the CVC/PAC within the patient, it is desirable to have a system and method that provides information concerning the location of the path and tip of the CVC/PAC within the patient anatomy in addition to the singular points for the tip and an anatomical reference point, as well as concerning the location of any complications regarding the intended position of the CVC/PAC within the patient anatomy.

SUMMARY OF THE DISCLOSURE

According to one aspect of an exemplary embodiment of the present disclosure, overall, the system and method of the present disclosure, with regard to a CVC model, assists in the confirmation of correct CVC tube position, the early detection of misplaced CVCs a that may result in a complication, and the early detection of potential complications from and/or interfering with CVC placement.

According to another aspect of an exemplary embodiment of the disclosure, additional benefits provided by the system and method are as follows:

- visualization of the course of the CVC and visualization of the CVC tip. These visualizations are crucial as they help the user determine if the CVC is placed properly.
- visualization of anatomical reference landmarks, e.g., carina and airways (trachea and the mainstems) of the area of the correct tip position.
- visualization of measurement of the Euclidian distance of the catheter (CVC) tip from the anatomical reference landmark (e.g., carina) and calculate the vertical and horizontal component measured in the patient coordinate system which can help the user determine if the CVC is placed properly where the axes and/or the units of measure of the patient coordinate system can be based on the anatomical structure (e.g., vertebral bodies or the trachea) present in the image to visualize the length of the CVC along these patient axes, optionally defined using patient-specific units of measure, and to project/illustrate the distance of the tip to the anatomical reference landmark (e.g., carina), along the patient's vertical axis and optionally with patient-specific units of measure.

display of the system-determined patient coordinate system and relevant measurement information visualization of measurement of the Euclidian distance of the tip from the desire position and/or anatomical reference landmark (e.g., carina) and calculate the vertical and horizontal component measured in the patient coordinate system to help the user determine if the CVC is placed properly and to triage images for radiologists and send alerts to bedside teams if these values are abnormal.

detect laterality of the catheter (CVC), tube or line and access site (IJ vs PICC vs subclavian vs femoral, among others), to help prevent improper documentation of lines.

comparison of the present image to prior images/measurements to help identify tube movement or migration between the images.

detection of common visualizable complications associated with CVC placement such as pneumothorax, hydrothorax, pneumomediastinum, pericardial effusion, and retained guide wires etc.

create and display of structured report on the catheter (CVC and/or PAC) position, malposition, complication and guidewire retention.

all of the above can be done for multiple CVC tubes present in the image

According to still a further aspect of an exemplary embodiment of the present disclosure, the system and method is based on Deep Learning (DL) technology of Artificial Intelligence (AI) to detect in an image, and visualize in a combined image formed of the image and information obtained from the image by the DL/AI:

the CVC and PAC lines and their tips.

the correct destination position and/or area of the tip of the CVC and PAC catheters.

the anatomical structures (e.g., carina and the airways (trachea and the mainstems) relevant to the destination position of the tip.

the determination of a patient coordinate system used to define the correct destination position and illustration of the vertical axis of the patient coordinate system.

the determination of a patient-specific unit of measure, e.g., distance, and illustration of positions of various anatomical and CVC/PAC structures using patient-specific units on the displayed vertical axis of the patient coordinate system.

position of misplaced catheters, for example but not exclusively, catheters in too high or too low positions, placed in wrong vessels, kink in the catheters, etc.

presence and locations of complications, for example but not exclusively pneumothorax and hemothorax.

presence and locations of guidewires in place, and/or other never events.

According to still another aspect of an exemplary embodiment of the present disclosure, the system and method will compute and visualize:

a horizontal axis of the patient coordinate system.

a Euclidean distance between the catheter tip and the desired position location/area and/or anatomical reference landmark (e.g., carina)

differences in Euclidian distance between catheter tip and desired anatomical reference landmark (e.g. carina) between x-rays obtained at different times vertical and horizontal components of the tip-carina Euclidean distance in the image coordinate system.

vertical and horizontal components of the tip-carina Euclidean distance in the patient coordinate system.

changes in the tip position compared to previous saved scans accessible by the system.

creation and display of warning messages related to the misplacement, complications and guidewire in place.

triage of detected critical conditions regarding CVC and/or PAC.

application to all types and intended use of Central Vein Catheters and Pulmonary Artery Catheters inserted from jugular, subclavian or peripheral (cubital, femoral) access points on all sides (left, right).

According to still another aspect of an exemplary embodiment of the present disclosure, a medical image processing system includes a display, a processor; and a memory storing processor-executable code that when executed by the processor causes receiving an image of a region of interest of a patient with a medical tube or line disposed within the region of interest, detecting the medical tube or line within the image, detecting a reference landmark within the region of interest within the image, wherein the reference landmark is internal to the patient, generating a patient coordinate system for the image, generating a combined image by superimposing a first graphical marker on the image that indicates a location of an end of the medical tube or line, and a second graphical marker on the image that indicates a position of the reference landmark, generating an indication in the combined image of a position of the end of the medical tube relative to the reference landmark using the patient coordinate system, and presenting the combined image on the display.

According to still another aspect of an exemplary embodiment of the present disclosure, an imaging system includes a radiation source, a detector alignable with the radiation source, a display for presenting information to a user, and a controller connected to the display and operable to control the operation of the radiation source and detector to generate image data, the controller including an image processing system having a processor and a memory storing processor-executable code that when executed by the processor causes receiving an image of a region of interest of a patient with a medical catheter, tube or line disposed within the region of interest, detecting the medical catheter, tube or line within the image, detecting a reference landmark within the region of interest within the image, wherein the reference landmark is internal to the patient, generating a patient coordinate system relative to an anatomy of the patient within the image, a combined image by superimposing a first graphical marker on the image that indicates an end of the medical catheter, tube or line, a second graphical marker on the image that indicates the reference landmark, and a third graphical marker the indicates the patient coordinate system, and displaying the combined image on the display.

According to still another aspect of an exemplary embodiment of the present disclosure, a method for medical image processing includes receiving, via a processor, an image of a region of interest of a patient with a medical catheter, tube or line disposed within the region of interest, detecting, via the processor, the medical catheter, tube or line within the image, detecting, via the processor, a number of reference landmarks within the region of interest within the image, wherein the number of reference landmarks are each internal to the patient, generating, via the processor, a patient coordinate system relative to the detected number of reference landmarks, generating, via the processor, a combined image by superimposing a first graphical marker on the image that indicates an end of the medical catheter, tube or line, and a second graphical marker on the image that indicates the reference landmark, and causing, via the processor, display of the combined image on a display.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings:

FIG. 1 is a schematic diagram of a condition comparator, according to an exemplary embodiment of the present disclosure.

FIG. 2 is a schematic diagram of an embodiment of a clinical progression analysis apparatus, according to an exemplary embodiment of the present disclosure.

FIG. 3 is a schematic diagram of an embodiment of a learning neural network, according to an exemplary embodiment of the present disclosure.

DETAILED DESCRIPTION OF THE DRAWINGS

Figure 4:
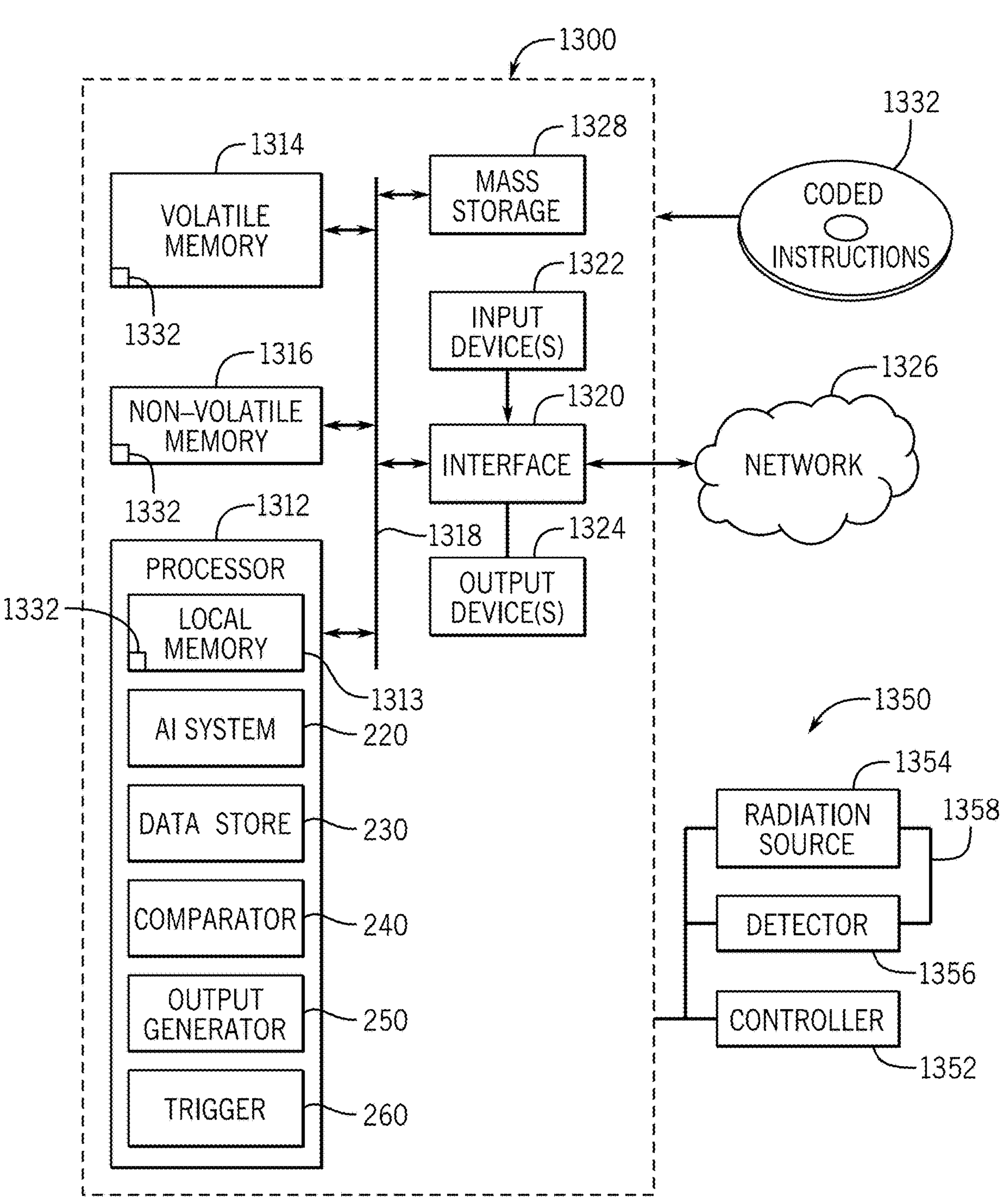
FIG. 4 is a schematic diagram of an embodiment of a processor platform structured to execute the example machine readable instructions to implement components disclosed and described herein, according to an exemplary embodiment of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Imaging devices (e.g., gamma camera, positron emission tomography (PET) scanner, computed tomography (CT) scanner, X-Ray machine, fluoroscopy machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, quality control, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine and/or deep learning can be used to help configure, monitor, and update the medical imaging workflow and devices.

Certain examples provide and/or facilitate improved imaging devices which improve diagnostic accuracy and/or coverage. Certain examples facilitate improved image reconstruction and further processing to provide improved diagnostic accuracy.

Certain examples provide an image processing apparatus including an artificial intelligence system (AI system). The AI system can detect, segment, and quantify pathology, for example. The AI system can be a discrete output of positive or negative for a finding, a segmentation, etc. For example, the AI system can instantiate machine learning and/or other artificial intelligence to detect, segment, and analyze a presence of a medical device (e.g., medically placed tube or line). For example, the AI system can instantiate machine learning and/or other artificial intelligence to detect an end of a medically placed tube or line, detect an anatomical reference landmark, determine a position of the medically placed tube or line relative to the reference or anatomical reference landmark, measure a distance between the end of the medically placed tube or line and the reference landmark, and determine whether the tube or line is properly placed.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Certain examples use neural networks and/or other machine learning to implement a new workflow for image and associated patient analysis including generating alerts based on radiological findings that may be generated and delivered at the point of care of a radiology exam. Certain examples use Artificial Intelligence (AI) algorithms to process one or more imaging exams (e.g., an image or set of images), and provide an alert based on the automated exam analysis. The alert(s) (e.g., including notification(s), recommendation(s), other action(s), etc.) may be intended for the technologist acquiring the exam, clinical team providers (e.g., nurse, doctor, etc.), radiologist, administration, operations, and/or even the patient. The alerts may be to indicate a specific or multiple quality control and/or radiological finding(s) or lack thereof in the exam image data, for example.

In certain examples, the AI algorithm can be (1) embedded within an imaging device, (2) running on a mobile device (e.g., a tablet, smart phone, laptop, other handheld or mobile computing device, etc.), and/or (3) running in a cloud (e.g., on premise or off premise) and delivers the alert via a web browser (e.g., which may appear on the radiology system, mobile device, computer, etc.). Such configurations can be vendor neutral and compatible with legacy imaging systems. For example, if the AI processor is running on a mobile device and/or in the "cloud", the configuration can receive the images (A) from the x-ray and/or other imaging system directly (e.g., set up as secondary push destination such as a Digital Imaging and Communications in Medicine (DICOM) node, etc.), (B) by tapping into a Picture Archiving and Communication System (PACS) destination for redundant image access, (C) by retrieving image data via a sniffer methodology (e.g., to pull a DICOM image off the system once it is generated), etc.

Certain examples provide apparatus, systems, methods, etc., to determine progression of a disease and/or other condition based on output of an algorithm instantiated using and/or driven by an artificial intelligence (AI) model, such as a deep learning network model, machine learning network model, etc. For example, the presence of a medically placed tube or line (e.g. chest tube, a nasogastric tube, endotracheal tube, vascular line, a peripherally inserted central catheter, a central venous access catheter, a pulmonary artery catheter, etc.) can be determined based on an output of an AI detection algorithm In addition, the placement of a catheter, medical tube or line within a region of interest (e.g., lung, stomach, vascular system, etc.) can be determined based on an output of an AI detection (e.g., whether the catheter is properly placed).

Thus, certain examples provide systems and method to detect a medically placed catheter, tube or line within a region of interest of a patient and whether the catheter, tube or line is properly placed within the region of interest based on an AI algorithm applied to a patient's data. An example method includes detecting a presence of a medically placed catheter, tube or line in an image; detecting an end of the medically placed catheter, tube or line in the image; detecting at least one anatomical reference landmark in the image; determining an anatomical or patient coordinate system using the at least one anatomical reference landmark, determining whether the end of the medically placed catheter, tube or line is properly placed relative to the anatomical reference landmark, providing a visual representation of the patient coordinate system and position of the end of the catheter, tube or line with respect thereto, and/or providing a notification for a physician as to whether the medically placed tube or line is properly placed relative to the anatomical reference landmark. In certain embodiments, the AI system may detect one or more anatomical reference landmarks, e.g., for defining a patient coordinate system, optionally in conjunction with patient-specific or patient defined axes and units/units of measure, employed in the determination of the proper placement of the catheter, tube or line relative to the patient coordinate system, detect the presence of the medically placed catheter, line or tube with reference to a patient coordinate system based on one or more anatomical reference landmarks, graphically mark the medically placed catheter, line or tube with a color graphical overlay on the patient coordinate system, detect an end (e.g., distal end) of the medically placed catheter, line or tube with reference to the patient coordinate system, graphically mark the end of the medically placed catheter, tube or line with reference to the patient coordinate system, graphically mark the one or more anatomical reference landmarks with reference to the patient coordinate system, calculate a distance between the end of the medically placed catheter tube or line and a desired position for the end, and/or calculate and provide a confidence metric (e.g., for the calculated distance, for the determination of the presence of the medically placed tube or line, for an accuracy in detecting the end of the tube or line, for an accuracy in detecting the anatomical reference landmark, etc.). The AI system is trained based on images with or without medically placed catheters, tubes or lines, images with properly placed catheters, tubes or lines, images with misplaced catheters, tubes or lines, images with the one or more anatomical reference landmarks, and/or images without the one or more of the one or more anatomical reference landmark.

For example, patients in a critical care setting receive chest x-rays (or other regions) to monitor the placement of a medically placed catheter, tube or line. If a catheter, tube or line is misplaced, the medical team may need to conduct a faster intervention properly placed the medical catheter, tube or line. An artificial intelligence system can detect a presence of the medically placed catheter, tube or line, detect an end of the medically placed catheter, tube or line, detect one or more anatomical reference landmarks, determine a patient coordinate system using the detected locations of the reference landmarks, and evaluate whether the catheter, tube or line is properly placed. An alert can be generated and output at a point of care, on a device (e.g., an imaging device, an imaging workstation, etc.) to notify and/or otherwise provide instructions (e.g., notification that a catheter is or is not properly placed or instruction to remove the catheter, tube or line, to shift the catheter, tube or line in a certain direction, etc.) to a clinical care team, for example.

The techniques describe herein provide a quicker means to determine if a medically placed catheter, tube or line is improperly placed and to illustrate the location for proper placement of the catheter, tube or line. This enables a faster intervention to ensure the catheter, tube or line is in an appropriate location for patient safety. In addition, it relieves some of the burden on the medical team providing assistance to the patient (especially those personnel who may be untrained or inexperienced).

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, classified and further annotated for object localization, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

Referring now to FIG. 1, as also disclosed in U.S. Pat. No. 11,410,341, (the '341 Patent), entitled System And Method For Visualizing Placement Of A Medical Tube Or Line, the entirety of which is expressly incorporated herein by reference for all purposes, an example condition comparator apparatus 100 is illustrated including a plurality of input 110, 115, (e.g., medical images or medical image data), an artificial intelligence (AI) system 120, and an output comparator 130. Each input 110, 115 is provided to the AI system 120, which classifies image and/or other information in the respective input 110, 115 to identify a condition in the input 110, 115 and to generate an indication of the identified condition based on the input 110, 115. In certain embodiments, the AI system 120 may classify images and/or other information in the respective input 110, 115 to identify a medically placed catheter, tube or line (e.g., chest tube, a nasogastric tube, endotracheal tube, vascular line, a peripherally inserted central catheter, a central venous access catheter, a pulmonary artery catheter, etc.) and to identify an anatomical reference landmark relevant to the catheter, tube or line and its desired placement. Using the example comparator apparatus 100, it can be determined whether an end of the catheter, tube or line is properly placed within a proper location or area, or anatomy/anatomical region of interest of the patient relative to patient coordinate system (FIG. 5) defined by one or more detected anatomical reference landmarks. In particular, both an end of the catheter, tube or line and an anatomical reference landmark may be located and a determination made as to whether the end of the tube or line is properly placed relative to the anatomical reference landmark through the use of the determined patient coordinate system. A distance may be measured between the end of the tube or line and the anatomical reference landmark using either absolute or patient-specific measurement or distance units via the patient coordinate system to determine whether the end of the catheter, tube or line is properly placed. A confidence metric (e.g., for the calculated distance, for the determination of the presence of the medically placed catheter, tube or line, for an accuracy in detecting the end of the catheter, tube or line, for an accuracy in detecting the anatomical reference landmark, etc.) may be calculated and/or provided via user-perceptible notification or stored for further reference. Further, a notification or alert may be provided as to whether or not the medically placed catheter, tube or line is properly placed. If the tube or line is not properly placed, further instructions may be provided via the patient coordinate system related to moving the catheter, tube or line in a certain direction.

In addition, using the example comparator apparatus 100, it can be determined whether there are any complications detected within the patient anatomy, with the detected complications taking the form of a nonbiological complication, e.g., a retained guidewire from the catheter, tube or line or other catheter malfunction, or a biological complication, e.g., a pneumothorax, hemothorax, etc. If detected, a notification can be provided to the physician of the presence and location of the complication relative to the patient coordinate system.

FIG. 2 illustrates an example clinical progression analysis apparatus 200 that can be constructed based on the example condition comparator apparatus 100 of FIG. 1. The example apparatus 200 includes a data source 210, an artificial intelligence (AI) system 220, a data store 230, a comparator 240, an output generator 250, and a trigger 260. Input 110, 115 can be provided by the data source 210 (e.g., a storage device, an imaging device, etc., incorporated in and/or otherwise connected to the apparatus 200, etc.) to the AI system 220.

The example AI system 220 processes input over time to correlate input from the data source 210 with a classification. Thus, the AI system 220 processes input image data and/or other data to identify a condition in the input data and classify that condition according to one or more states (e.g., catheter, tube or line present, catheter, tube or line not present, anatomical reference landmark(s) present, anatomical reference landmark(s) not present, determination of patient coordinate system (FIGS. 6 and 7) using anatomical reference landmarks and/or anatomical markers to define proper placement of catheter, tube or line, catheter, tube or line placed correctly, catheter, tube or line misplaced, complication present, complication not present) as specified by an equation, a threshold, and/or other criterion. In certain embodiments, the AI system 220 processes input image data and/or other data to detect a medically placed catheter, tube or line, to determine whether an end of the medically placed catheter, tube or line is properly placed, to identify the location of the end of the catheter, tube or line relative to a patient coordinate system based on anatomical reference landmarks and/or anatomical markers of the patient, and to determine the presence of any complications in the patient anatomy concerning the proper placement of the end of the catheter, tube or line. Output of the AI system 220 can be stored in the data store 230, for example.

Over time, classifications made by the AI system 220 with respect to the same type of input 110, 115 from the data source 210 (e.g., lung MR images of the same patient taken at times t0 and t1, etc.) can be generated and stored in the data store 230. The classifications are provided to the comparator 240, which compares a classification at two or more different times at two or more different times (e.g., prior to insertion of the catheter, tube or line and after the insertion of the catheter, tube or line) to identify the medically placed catheter, tube or line and determine whether the end of the medically placed catheter, tube or line is properly placed. For example, at time t0 the catheter, tube or line may not present in the region of interest and at time t1 or a later time end of the catheter, tube or line may be placed in a location (which may or may not be properly placed) within the region of interest/acceptable area defined using the patient coordinate system.

The comparator 240 provides a result indicative of the trend/progression. In certain embodiments, the comparator 240 provides a result indicative of a placement of an end of a medically placed catheter, tube or line. The output generator 250 transforms that result into an output that can be displayed, stored, provided to another system for further processing such as an alert, an order, an adjustment in patient care, (e.g., a point of care alert system, an imaging/radiology workstation, a computer-aided diagnosis (CAD) processor, a scheduling system, a medical device, etc.), etc.

The trigger 260 coordinates actions among the data source 210, the AI system 220, the data store 230, the comparator 240, and the output generator 250. The trigger 260 can initiate input of data from the data source 210 to the AI system 220, comparison of results from the data store 230 by the comparator 240, output by the output generator 250. Thus, the trigger 260 serves as a coordinator among elements of the apparatus 200.

FIG. 3 illustrates an example implementation of the AI system 220 to process image data to be used by an AI model to quantify a condition (e.g., placement of a catheter, tube or line). The example implementation of the AI system 220 enables annotation of one or more images including an organ region and a region of interest within the organ region. The example AI system 220 of FIG. 3 includes an image segmenter 1010, a mask combiner 1020, and an example condition comparator 1040.

The example image segmenter 1010 is to identify a first mask and a second mask in an input image. For example, the image segmenter 1010 processes the image to segment a region of interest within an organ region identified in the image to obtain a first mask. The first mask is a segmentation mask is a filter that includes the region of interest in the image and excludes the remainder of the image. The mask can be applied to image data to exclude all but the region of interest, for example. The mask can be obtained using a convolutional neural network model, for example, a generative adversarial network, etc. The image segmenter 1010 further processes the image to segment the organ region according to one or more criterion to obtain a second mask. For example, the second mask can represent the organ region, an area of the organ region outside the region of interest, etc.

For example, if the organ region is a lung (and the surrounding area such as the trachea), and the region of interest is a tube or line identified in the trachea, the first mask is generated to identify the medically placed tube or line, and the second mask is generated to identify the entire organ region. In another embodiment, if the organ region is a stomach, and the region of interest is a tube or line identified in the stomach, the first mask is generated to identify the medically placed tube or line, and the second mask is generated to identify the entire organ region. In a further embodiment, if the organ region is a heart (and the surrounding area such as veins or other vasculature), and the region of interest is a catheter or line identified in a vein or other vasculature near the heart, the first mask is generated to identify the medically placed catheter or line, and the second mask is generated to identify the entire organ region. Thus, in regard to a medically placed catheter, tube or line, a first mask is generated for the catheter, tube or line and a second mask is generated for the entire organ region where the catheter, tube or line is placed (e.g., vasculature system, heart, lung, stomach, trachea, chest, pleural space, etc.).

The example combiner 1020 combines the first mask and the second mask and associated areas with annotation terms in the image. Annotations can be relative qualification terms to produce quantification, for example. For example, mask areas can be combined with descriptive terms such as foggy, patchy, dense, etc., to compute relative density values for the region of interest and organ region in the image. Image areas (e.g., areas of frontal and lateral images, etc.) can be combined to produce a volume metric, for example.

The example distance computer 1030 determines a distance between an end of an identified tube or line and an anatomical reference landmark (or determines a position of the tube or line relative to the reference landmark). The distance can be computed by identifying one or more attributes, structures or markers within the image, such as the carina, transverse process, and/or the spine.

In one exemplary embodiment for operating the example distance computer 1030, a patient coordinate system 1700 (FIGS. 6 and 7) that is employed to provide the distance information can be formed using the anatomy present in the image 1701 and/or 1702 in a number of manners. In a first exemplary embodiment, the AI system 220, example distance computer 1030 and/or processor 1312 (FIG. 4) can define one or more local or patient coordinate systems 1700 near the carina 1712 by detecting and displaying the midpoints of one or more identified or first anatomical markers within the anatomy represented within the image 1701, e.g., the vertebral bodies/vertebrae 1704 of the patient and the "vertical axis" 1706 they form. The AI system 220 and/or processor 1312 can similarly define the "horizontal axis" 1708 formed by the mid-point of one or more other or second anatomical markers, e.g., the transverse processes 1710 of the vertebral bodies/vertebrae 1704. These horizontal and vertical axes 1708,1706 will be generated at each vertebral level. This embodiment selects the local vertical axis 1706 to be used to perform the measurements based on one or more the vertebrae 1704 that are close to the location of the carina 1712 and/or the end of the device. The detected horizontal and vertical axes 1706,1708 may be fine-tuned to ensure that the two directions are exactly perpendicular to each other. Such a local or patient coordinate system 1700 may be useful in case of severe spine disorders, where the shape of the spine is significantly different from a straight line, and thus the local "vertical" axis may be substantially different at different locations within the patient's anatomy.

According to another exemplary embodiment of the disclosure, to define a vertical axis 1706 for chest images by employing a spine axis, the AI system 220/processor 1312 for the associated anatomical marker(s) can identify as the first anatomical markers the midpoint of the upper edge of the most superior thoracic vertebra 1704, which is usually the first thoracic vertebra, and the midpoint of the lower edge of the most inferior thoracic vertebra 1704, which is usually the twelfth thoracic vertebra, to enable the line extending therebetween to function as the vertical axis 1706 for the coordinate system 1700. Further, to define the horizontal axis 1708, the AI system 220/processor 1312 can compute a straight line that is normal the vertical axis 1706 that extends through the carina 1712, e.g., the second anatomical marker. In a modified version of this process, the AI system 220/processor 1312 can detect the edges of multiple vertebrae 1704 and compute the midpoint of each vertebrae 1704, then fit a straight line to this set of points. In this process the AI system 220/processor 1312 can determine an overall angle of a patient rotation, and adapt the utilized coordinate system to the patient position.

According to still another exemplary embodiment of the present disclosure for determination of a vertical axis 1706 for chest images, the AI system 220/processor 1312 may use as the associated anatomical marker the location of the trachea 1714 which is detected by the AI system. One potential embodiment defines a vertical axis between the carina 1712 (e.g., the first anatomical marker) and the most superior midpoint of the trachea 1714 (e.g., the second anatomical marker). An alternative embodiment segments the entire trachea 1714 and fits a straight line to the detected trachea points. To define the horizontal axis 1708, the AI system 220/processor 1312 computes a straight line normal to the vertical axis 1706 going through the carina 1712, e.g., the second anatomical marker.

In still another exemplary embodiment of the present disclosure, the patient coordinate system 1700 can be determined by the AI system 220/processor 1312 utilizing a deep learning regression model that predicts the patient rotation angle directly from the entire x-ray image, e.g., image 1701.

The example condition comparator 1040 utilizes the patient coordinate system to compares the distance or measured positions of the tip of the catheter to a preset distance or desired position for the type of catheter, tube or line and/or anatomy/anatomical area/region of interest where the catheter, tube or line is placed (e.g., in accordance with predetermined rules). The preset distances may be provided in absolute units, or in patient specific units (to be described). Based on this comparison, the example condition comparator 1040 can determine whether the end of the catheter, tube or line is properly placed relative to the anatomical reference landmark. This determination and the patient coordinate system utilized to make the determination can be annotated onto the medical image in order to provide direct and clear information to the physician regarding the location of the catheter and catheter tip, as well as any positional changes that are required to be made to the catheter tip for proper placement and/or to detect any movement of the tip of the catheter over time when separate images of the region of intertest and the catheter are obtained at different times.

Thus, the AI system 220 can be configured to annotate a medical image or set of related medical image(s) for AI/machine learning/deep learning/CAD algorithm training, to quantify conditions. Such methods are consistent, repeatable methodologies which could replace common subjective methods of today, enabling automatic, accurate detection of the presence of a medically placed catheter, tube or line and its placement.

While example implementations are illustrated in conjunction with those disclosed in U.S. Pat. No. 11,410,341, (the '341 Patent), entitled System And Method For Visualizing Placement Of A Medical Tube Or Line, the entirety of which is expressly incorporated herein by reference for all purposes, the disclosed elements, processes and/or devices illustrated in the '341 patent can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor (s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 5:
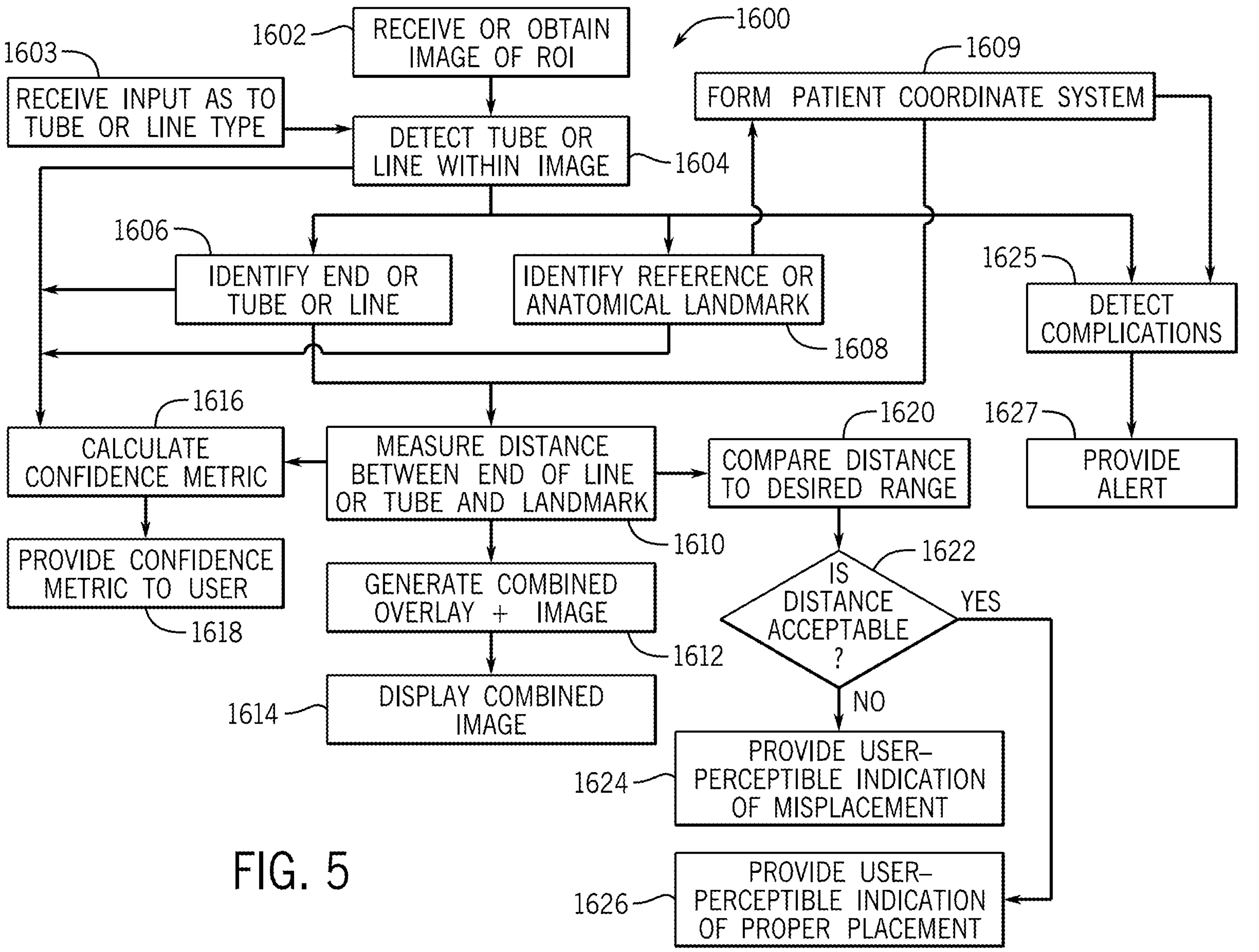
FIG. 5 is a is a flow diagram of an embodiment of a method for determining a placement of a medically placed tube or line within a region of interest, according to an exemplary embodiment of the present disclosure.

FIG. 4 is a block diagram of an example processor platform 1300 structured to executing the instructions of at least FIG. 5 to be described to implement the example components disclosed and described herein. The processor platform 1300 can be, for example, a server, a personal computer, a mobile device (e.g., a cell phone, a smart phone, a tablet such as an iPad™), a personal digital assistant (PDA), an Internet appliance, or any other type of computing device, such as a computing device forming a part of a digital imaging system, such as an imaging system 1350 incorporating the processor platform 1300 as a controller 1352, or as a part of or operably connected to the controller 1352. The imaging system 1350 also includes a radiation source 1354, e.g., an X-ray source, and a detector 1356 alignable with the radiation source 1354, such as by being mounted to a gantry 1358 with the radiation source 1354, that can be selectively positioned and operated by the controller 1352 to obtain the image data utilized by the processor platform 1300 for producing the anatomy or object image(s) 1701 (FIG. 6) of the region of interest and combined images 1702 (FIG. 7) for presentation on a connected output device or display 1324.

The processor platform 1300 of the illustrated example includes a processor 1312. The processor 1312 of the illustrated example is hardware. For example, the processor 1312 can be implemented by integrated circuits, logic circuits, microprocessors or controllers from any desired family or manufacturer.

The processor 1312 of the illustrated example includes a local memory 1313 (e.g., a cache). The example processor 1312 of FIG. 4 executes the instructions of at least FIG. 5 to implement the systems, infrastructure, displays, and associated methods of training and implementing the method 1600, such as the example data source 210, AI system 220, data store 230, comparator 240, output generator 250, trigger 260, etc. The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a clock controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 1324 are also operably connected, e.g., wired or wirelessly, to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIG. 4 may be stored in the mass storage device 1328, in the volatile memory 1314, in the non-volatile memory 1316, and/or on a removable tangible computer readable storage medium such as a CD or DVD.

A flowchart representative of example machine readable instructions for implementing components disclosed and described herein in an exemplary method 1600 are shown in conjunction with at least FIG. 5. In the examples, the machine readable instructions include a program for execution by a processor such as the processor 1312 shown in the example processor platform 1300 discussed in connection with FIG. 4. The program may be embodied in machine readable instructions stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowchart illustrated in conjunction with at least FIG. 5, many other methods of implementing the components disclosed and described herein may alternatively be used. For example, the order of execution of the blocks may be changed, and/or some of the blocks described may be changed, eliminated, or combined. Although the flowchart of at least FIG. 5 depicts an example operation in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIG. 5 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIG. 5 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As mentioned above, these techniques may be utilized to identify a medically placed tube or line and to determine if medically placed tube or line is properly placed. For example, the medically placed tube or line may be an endotracheal tube and the proper placement of the endotracheal tube within the trachea (e.g., relative to the *canna*) may be determined. In another example, the medically placed tube or line may be a nasogastric tube and the proper placement of the nasogastric tube within the stomach may be determined. In a further example, the medically placed tube or line may be a vascular line (e.g., PICC line, central venous access catheter (CVC), pulmonary artery catheter (PAC), etc.) and the proper placement of the vascular line within a certain vasculature may be determined. In yet a further example, the medically placed tube line may be a chest tube and the proper placement of the chest tube within the chest (in particular, the plenum space) may be determined. These examples are intended to be non-limiting, and any other tube or line inserted within a region of interest of body may be identified and its proper placement determined.

FIG. 5 is a flow diagram of an embodiment of a method 1600 of operation of the AI system 220 and/or the processor 1312 for determining a placement of a medically placed catheter, tube or line within a region of interest. One or more steps of the method may be performed by the processor platform 1600 in FIG. 4. One or more steps may be performed simultaneously or in a different order from that illustrated in FIG. 5. The method 1600 includes receiving or obtaining an image 1701 (e.g., chest image) of a patient that includes a region of interest (ROI) (block 1602). The image may include a medically placed catheter, tube or line inserted within the region of interest. The image may be provided while the patient has the catheter, tube or line inserted. The method 1600 also includes receiving or obtaining an input regarding the type of catheter, tube or line to be detected (e.g., CVC or PAC) and/or the region of interest for the catheter, tube or line to be inserted within (e.g., central vein or artery) (block 1603). The input may be a user defined distance or rules for defining the proper placement of the end of the medically placed catheter, tube or line relative to a reference or anatomical location, e.g., the carina. In certain embodiments, the input may simply be the type of catheter, tube or line and/or the desired region of interest for the catheter, tube or line to be properly placed within. Based on this input, certain defined distances or rules (e.g., left, right, above, and/or below a specific anatomical location) may be utilized that define a proper placement of the end of the specific catheter, tube or line within a specific region of interest (e.g., a specific distance range above the carina for a CVC or PAC). The method 1600 also includes detecting the catheter, tube or line within the image (block 1604) utilizing the techniques described above. The method 1600 includes identifying an end (e.g., distal end) of the catheter, tube or line within the region of interest in the image (block 1606). The method 1600 also includes identifying an anatomical reference landmark within the image (block 1608). The anatomical reference landmark will vary based on the type of catheter, tube or line utilized and the region of interest that the catheter, tube or line is disposed within. For example, for an endotracheal tube, the anatomical reference landmark may be the carina of the trachea. For a nasogastric tube, the anatomical reference landmark may be a location within the stomach below the gastroesophageal junction. For a vascular line, the anatomical reference landmark may be the carina of the trachea or a location within the superior vena cava, the inferior vena cava, or proximal right atrium, among others. The determination of the location of the anatomical reference landmarks also includes the determination of the anatomical markers or structures utilized in forming the patient coordinate system 1700 (block 1609), which may include and/or be separate from the anatomical reference landmark previously determined based on the type of catheter, tube or line utilized and the region of interest within the image 1701, according to one or more of the processes described previously.

Upon identifying the end of the catheter, tube or line, the anatomical reference landmark(s) and the patient coordinate system 1700, the method 1600 includes measuring a distance between the end of the catheter, tube or line and an acceptable location or range of locations for the tip relative to the anatomical reference landmark (block 1610). The distance can be illustrated as a Euclidian length between the tip and the desired location or range of locations, and/or as individual horizontal and vertical distance components relative to the patient coordinate system 1700. The method 1600 includes generating a combined image 1702 (FIGS. 6 and 7) with indications of the end of the catheter, tube or line, the anatomical reference landmark, the patient coordinate system and/or the measured distance identified in the combined image 1702, such as in the form of an overlay 1703 (block 1612). Generating the combined image 1702 including the x-ray image 1701 and the overlay 1703 includes superimposing various markers on the received image 1701 of the patient. For example, a color coding (e.g., color coded graphical overlay) may be superimposed on the detected catheter, tube or line 1705. In certain embodiments, the patient may include more than one catheter, tube or line and the catheter, tube or line of interest is color coded. A graphical marker may be superimposed on the image to indicate the end 1707 of the catheter, line or tube. Another graphical marker may be superimposed on the image to indicate the anatomical reference landmark location 1709. The graphical markers may include the same shape or different shapes. Non-limiting examples of the shapes may be an open circle or other elliptical shape, open rectilinear shape, open triangular shape, or another shape. The different graphical and the tube may be color coded with different colors. For example, the graphical marker for the tube or line, the graphical marker for the anatomical reference landmark, and the tube or line may be green, blue, and yellow, respectively. A graphical marker may also be superimposed on the image indicating the patient coordinate system 1700, a distance 1720 between the end of the tube or line and the anatomical reference landmark when a distance is calculated, and the horizontal component 1722 and vertical component 1724 of the distance 1720 as determined relative to the patient coordinate system 1700. The graphical marker for the distance may also include the measurement value. The method 1600 further includes displaying the combined image on a display (block 1614). The combined image may be displayed in real-time to the medical personnel enabling them to adjust the placement of the tube or line if need be. In certain embodiments, the combined image may be displayed as a DICOM image.

In certain embodiments, the method 1600 includes calculating one or more respective confidence metrics (block 1616). The confidence metrics may be for the calculated distance, for the determination of the presence of the medically placed device, e.g., tube or line, for an accuracy in detecting the end of the tube or line, and/or for an accuracy in detecting the anatomical reference landmark. The confidence metric may include a confidence level or confidence interval. The confidence metric may be stored for future reference. In certain embodiments, the method 1600 may include providing one or more of the confidence metrics to a user (block 1618). For example, the confidence metrics may be displayed on the combined image or provided on a separate device (e.g., user's device). In certain embodiments, the confidence metrics may be written into a standard or private information tag (e.g., DICOM) and made visible in subsequent information systems that the image is sent to (e.g., PACS).

In certain embodiments, in determining whether the end of the medically placed tube or line is placed properly (e.g., via the artificial intelligence and/or deep learning networks models), the method 1600 includes comparing the measured distance between the end of the tube or line and the anatomical reference landmark to a desired threshold (block 1620), such as stored in memory 1328 for proper placement of the particular medical device(s) in the associate procedure (s), and determining if the distance is acceptable (block 1622). The desired threshold may represent an acceptable range for the distance between the end of the tube or line and the anatomical reference landmark for the tube or line to be correctly placed. For example, for an endotracheal tube, the desired threshold may be 2 to 3 centimeters (cm) above the carina (e.g., anatomical reference landmark). For a nasogastric tube, the desired threshold may be a range of distance below the gastroesophageal junction. For a central venous catheter (CVC), the desired threshold may be a range of distance above or below the reference landmarks, such as the carina or right atrium. If the measured distance is not acceptable, the method 1600 includes providing a user-perceptible indication of misplacement (block 1624). The indication may be provided on the display where the combined image is displayed or provided on another device (e.g., the user's device). The indication may be text stating that the tube or line is misplaced. In certain embodiments, the text may be more specific and state the tube or line is too high (e.g., greater than the desired 2 to 3 cm for the endotracheal tube placement) or too low (e.g., less than the 2 cm for the endotracheal tube placement). In certain embodiments, the text may provide further instructions (e.g., to raise or lower the end of the tube or line a certain distance). In some embodiments, the text may be color coded (e.g., in orange or red) to further indicate the misplacement. In some embodiments, the indication may be provided via color coding of one or more graphical markers or the tube or line displayed on the combined image. For the example, one or more of the graphical markers (e.g., for the end of tube or line, for the anatomical reference landmark, and/or the indication of the measured distance there between) and/or the tube or line may be color coded a specific color (e.g., red or orange) to indicate the misplacement. Alternatively or in addition, one or more of the graphical markers may flash if the tube or line is misplaced. If the measured distance is acceptable, the method 1600 includes providing a user-perceptible indication of proper placement of the tube or line (block 1626). The indication may be provided on the display where the combined image is displayed or provided on another device (e.g., the user's device). The indication for proper placement may be text stating the tube or line is properly placed. In certain embodiments, the indication for proper placement may be provided via color coding one or more graphical markers of the tube or line displayed on the combined image (e.g., all the graphical markers and/or the tube or line may be color coded green). In certain embodiments, the indication of proper placement or misplacement may be written into a standard or private information tag (e.g., DICOM) and made visible in subsequent information systems that the image is sent to (e.g., PACS). In certain embodiments, the determination as to whether the end of the medically placed tube or line may be manually done by the medical personnel viewing the displayed combined image.

In still another exemplary embodiment of the method, 1600, in block 1625 the AI system 220 and/or processor 1312 can also be configured to detect any complications, e.g., non-biological complications, such as a never-events, including but not limited to a retained guidewire, and/or biological complications, including but not limited to pneumothoraxes, hemothoraxes, etc., in part using the information previously determined regarding the tube or line position, the location of the end of the tube or line, the applicable anatomical reference landmarks, and/or the patient coordinate system. If one or more complications are detected by the AI system 220 and/or processor 1312, in block 1627 the user/physician can be provided with an alert regarding the presence, location and type of complication detected, such as by employing a user-perceptible indication similar to that discussed with regard to block 1626.

Figure 6:
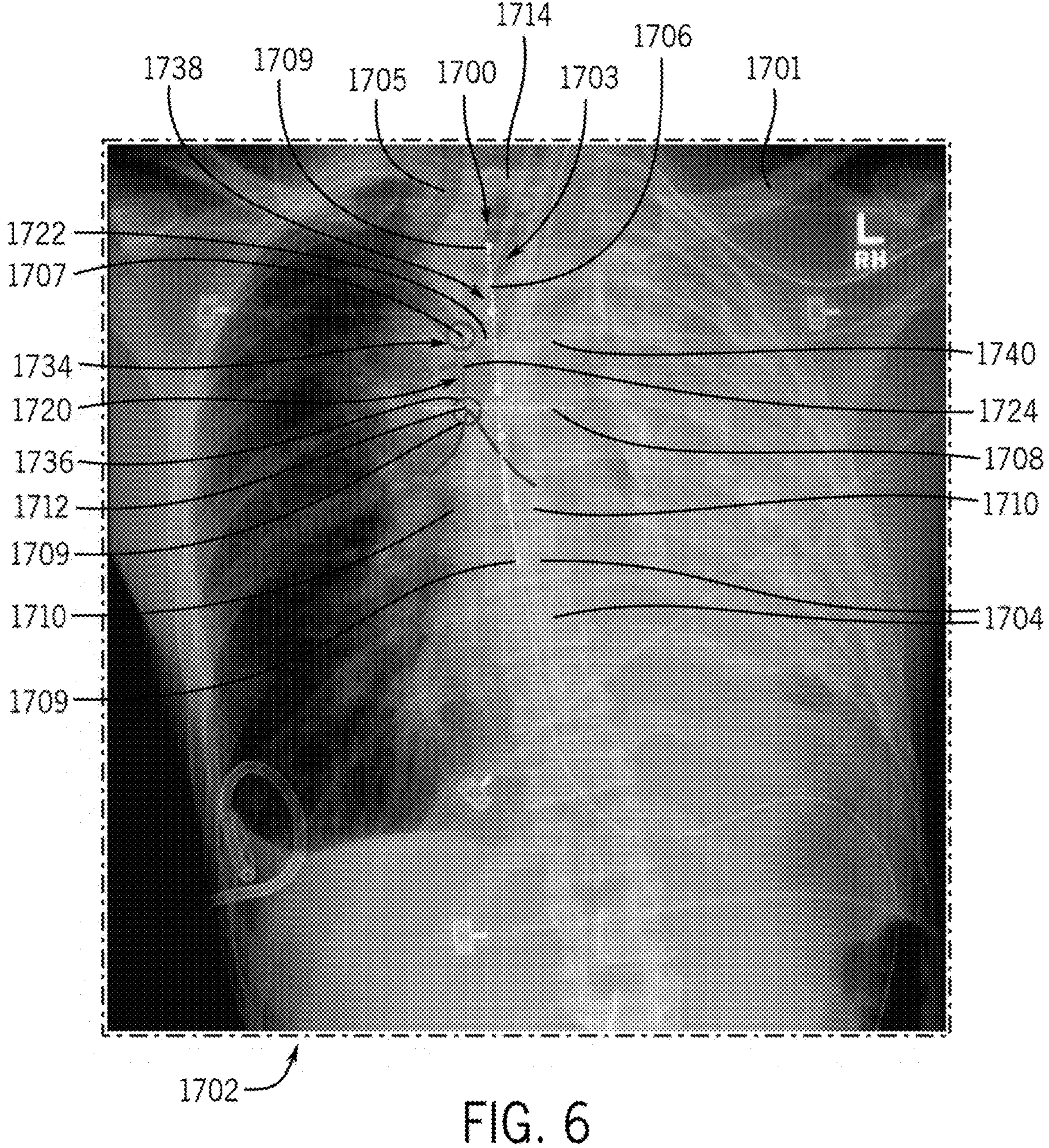
FIG. 6 is a first example of a combined image identifying a catheter within a patient, according to an exemplary embodiment of the present disclosure.
Figure 7:
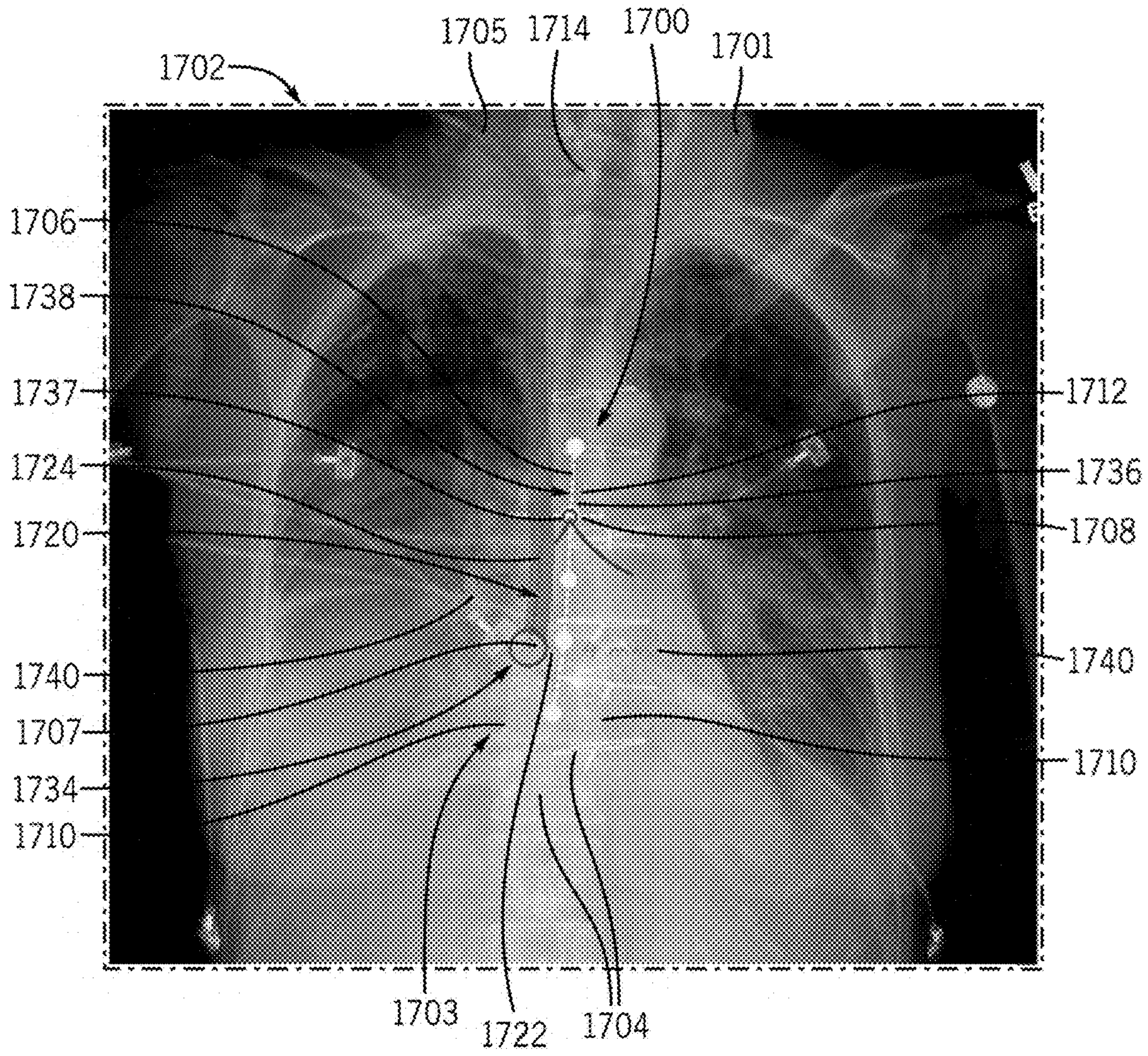
FIG. 7 is a second example of a combined image identifying a catheter within a patient, according to an exemplary embodiment of the present disclosure.

FIGS. 6 and 7 are exemplary embodiments of combined images 1702 (e.g., DICOM image) such as that produced by the method 1600 in block 1612 identifying a catheter, tube or line 1705 within a patient that may be displayed on a display or other output device 1324. As depicted, the combined images 1702 are chest images 1701 of a patient showing an CVC 1705 disposed within the central vein and including an overlay 1703. The overlay 1703 includes a first graphical marker 1734 (e.g., circle) overlaid on the chest image 1701 indicates the location of the tip or end 1707 of the CVC 1705. A second graphical marker 1736 (e.g., solid circle with chevron) overlaid on the chest image indicates a desired placement location 1737 for the tip 1707, which can be determined relative to or the same as a reference or anatomical landmark location 1709 (e.g., vertebrae 1704, carina 1712, trachea 1714, which can be the same or different for each anatomical location 1709). A third graphical marker 1738 indicates a distance 1720 (e.g., Euclidian distance) between the end 1707 of the CVC 1705 and the second graphical marker 1736. A numerical value 1740 for the measured distance accompanies the graphical marker 1738. Also illustrated in the overlay 1703, optionally as part of the third marker 1738, is the patient coordinate system 1700, including the vertical axis 1706, the horizontal axis 1708, and the horizontal component 1722 and vertical component 1724 of the distance 1720 as determined relative to the patient coordinate system 1700 and accompanied by their independent numerical values 1740.

The exemplary embodiments of the present disclosure may also use different methods to determine the patient coordinate system 1700 and distance unit(s) to be used during calculations. In the prior described embodiments for the AI system 220 and/or processor 1312 and associated method 600, the absolute distance units, e g, millimeters (mm), centimeters (cm), inches (in), etc., can be used to provide the distance 1720, e.g., the horizontal component 1722 and vertical component 1724 of the distance 1720 between the tip 1707 and the anatomical landmark 1709 as determined relative to the patient coordinate system 1700 and accompanied by their independent numerical values 1740 based on the known geometrical magnification of the image 1701, as shown in FIGS. 6 and 7.

Figure 10:
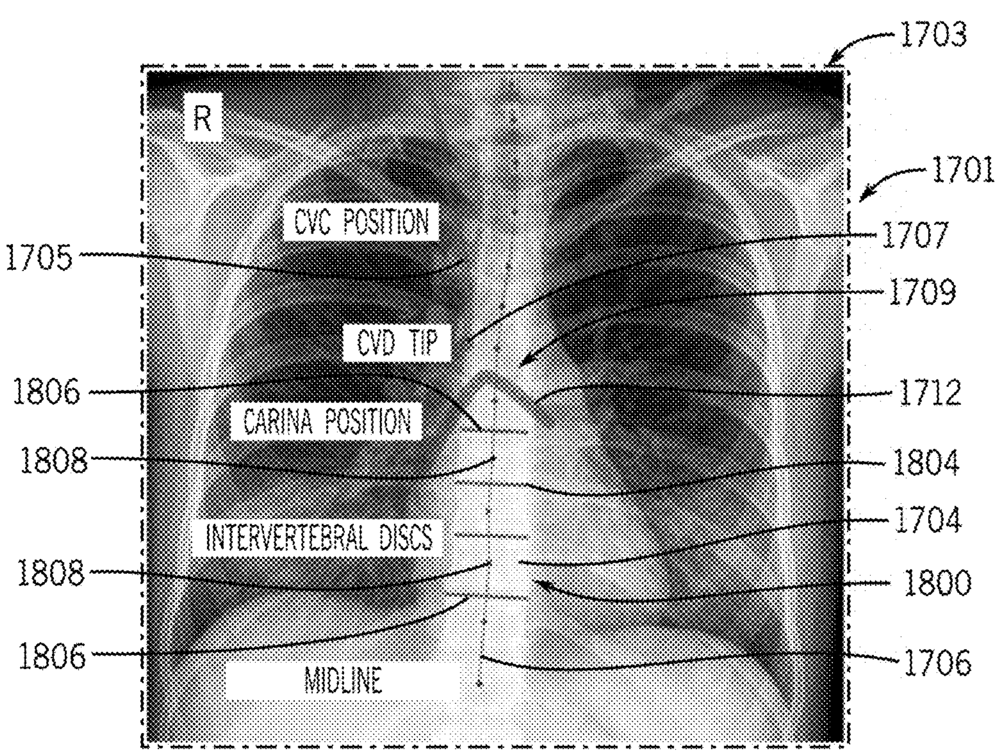
FIG. 10 is a schematic view of a combined image including anatomical reference points used to define a patient-specific distance units, according to an exemplary embodiment of the present disclosure.
Figure 11:
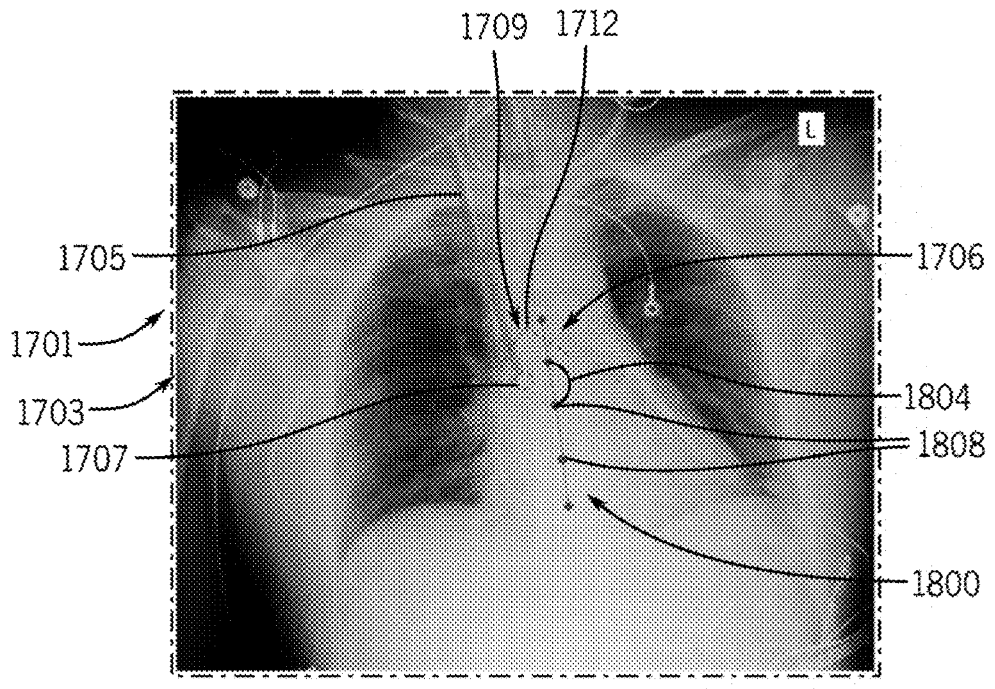
FIG. 11 is a schematic view of a combined image identifying a catheter within a patient employing patient-specific measurement units, according to an exemplary embodiment of the present disclosure.

However, the assessment of the proper location of the CVC 1705 may be influenced by the positioning and/or size of the patient. For example, the patient may be rotated with respect to the primary axes and/or plane of the image 1701, and therefore the measurement of a vertical distance between points of interest, such as the tip 1707 of the CVC 1705 and the one or more anatomical reference landmarks, e.g., the carina, should most preferably be made in a direction adapted to the position and/or orientation of the patient. In addition, the optimal distance and/or position of the CVC 1705 may depend on the patient size, such that a distance that is optimal for a large adult may be too long for a small or pediatric patient. To account for these differences in the sizes of the individual patients, the distance between the CVC 1705 and/or tip 1707 and the landmarks 1709 may be measured in units 1800 adapted to the particular patient size. More specifically, in another exemplary embodiment for the AI system 220/processor 1312 and associated method 600, some anatomical reference locations 1709, such as vertebrae 1704, may be located within the image 1701, and their distance may be used to define patient-specific distance units 1800. For example, with reference now to FIGS. 10 and 11, the distance between the centerpoints 1802 of consecutive intervertebral disks 1806 represented within the image 1701 can be defined as a patient-specific vertebral body unit 1804. The distance between the desired location 1737 and/or the anatomical location 1709, e.g., the carina 1712, and the CVC tip 1707 may then be measured in patient-specific vertebral body units 1804 as proposed in Baskin et al., Cavoatrial Junction and Central Venous Anatomy: Implications for Central Venous Access Tip Position, Journal of Vascular Interventional Radiology 2008; 19:359-365, the entirety of which his expressly incorporated herein by reference for all purposes. In addition, the patient-specific distance units 1800 can also be utilized in conjunction with the patient midline or vertical axis 1706 of the patient coordinate system 1700, as defined in one exemplary embodiment by the centerpoints 1802 of the vertebrae 1704, to help determining whether the tip 1707 is located to the left or to the right of the midline 1706 with a horizontal component 1722 defined with the patient-specific units 1800. In addition, the AI 220 and/or processor 1312 and associated method 600 can illustrate the location of the intervertebral disks 1806 that indicate the magnitude of the patient-specific vertebral body unit 1804, and allows the user to evaluate the distance, i.e., either the horizontal component 1722 or the vertical component 1724 or both, relative to the horizontal axis 1708 and/or vertical axis 1706 in these patient-specific vertebral body units 1804. In another embodiment, the AI system 220 and/or processor 1312 can detect and display the centers 1802 of the intervertebral disks 1806 as points 1808 presented on the image 1701 on the display 1324 and connected to form a partial midline or vertical axis 1706 of the patient. In this manner, the separation/distance between the points 1808 indicates the vertebral body unit 1804 and the displayed points 1808 may serve as a patient-specific ruler to assess the position of the CVC 1705 using the vertebral body units 1804 represented on the midline/vertical axis 1706.

In certain other embodiments, a confidence metric, such as that calculated in block 1616 of the method 1600, in the measured distance generated by the artificial intelligence is also displayed (e.g., as depicted a confidence level). In certain embodiments, the tube 1705, the first graphical marker 1734, and/or the second graphical marker 1736 may be color coded (e.g., yellow, green, and red). The combined image 1702 can include a header (not shown) that includes information related to the image 1702. For example, the header can include information on the type of tube or line 1705 (e.g., CVC), whether the placement of the tube is proper or not relative to predetermined placement parameters, such as stored in the memory 1313, and the calculated distance 1720 between the end 1707 of the tube 1705 and the desired placement location 1737 and/or anatomical location 1709. In certain embodiments, the header may include an indication as to whether the tube or line was detected. In certain embodiments, one or more confidence metrics may be displayed on the combined image 1702, e.g., confidence metrics for one or more of the calculated distance, the determination of the presence of the medically placed tube or line, the accuracy in detecting the end of the tube or line, and/or the accuracy in detecting the anatomical reference landmark.

Figure 8:
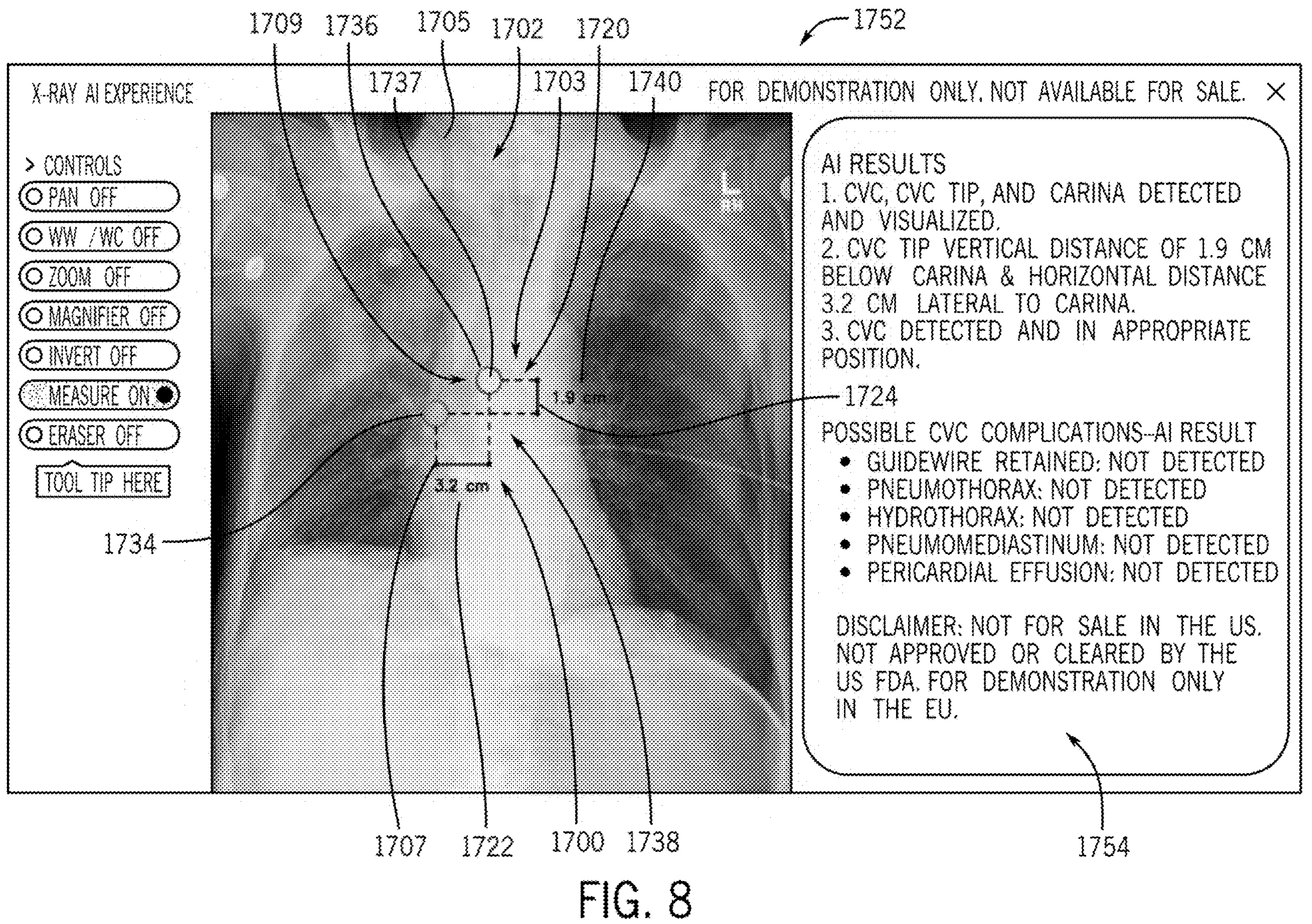
FIG. 8 is a first schematic diagram of a user interface having a combined image identifying a catheter within a patient, according to an exemplary embodiment of the present disclosure, according to an exemplary embodiment of the present disclosure.
Figure 9:
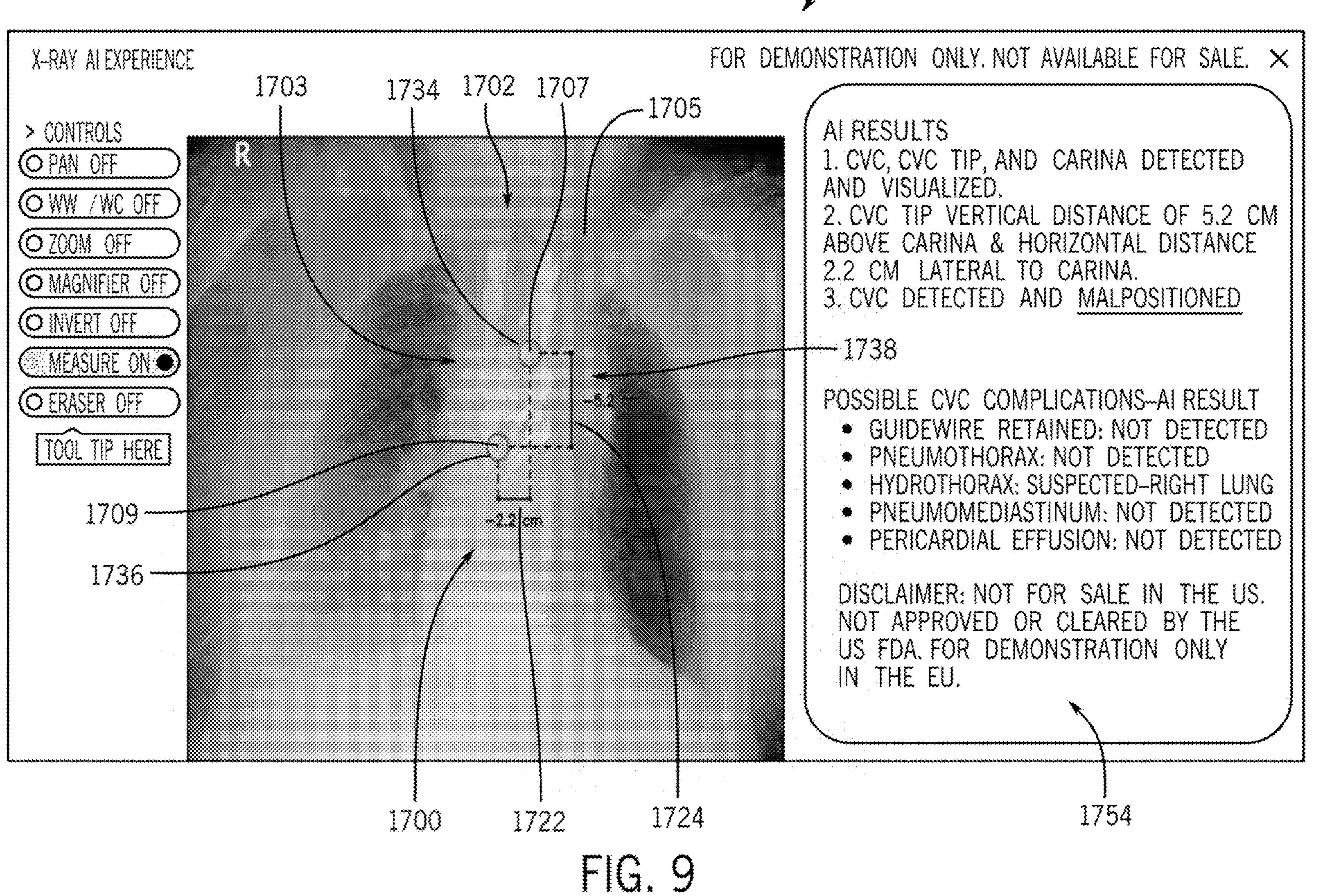
FIG. 9 is a second schematic diagram of a user interface having a combined image identifying a catheter within a patient, according to an exemplary embodiment of the present disclosure.

FIGS. 8 and 9 are schematic diagrams of exemplary embodiments of a user interface 1752 presented in conjunction with a combined image 1702 identifying a catheter 1705, tube or line within a patient that may be displayed on a display or output device 1324. As depicted in FIG. 8, the combined image 1702 is a chest image 1701 of a patient showing a CVC 1705 disposed within the central vein. A first graphical marker 1734 (e.g., circle) overlaid on the chest image 1701 indicates the location of the end 1707 of the CVC 1705. A second graphical marker 1736 (e.g., circle) overlaid on the chest image 1701 indicates a desired placement location for the end 1707 and/or a reference or anatomical location 1709 (e.g., carina). A third graphical marker 1738 indicates a distance 1720, including a horizontal component 1722 and a vertical component 1724, between the end 1707 of the CVC 1705 and the desired location and/or reference or anatomical location 1709. A numerical value 1740 for the measured distance 1720 and/or the components accompanies the graphical marker 1738. As mentioned above, in certain embodiments, the tube 1705, the graphical marker 1734 and/or the graphical marker 1736 may be color coded (e.g., yellow, green, and red). The user interface 1752 includes controls 1753 for altering the presentation of the image 1702 on the display 1324 and one or indications 1754 of an analysis by the AI 120/220 and/or processor 1312 regarding one or more the detection of the CVC 1705, CVC tip 1707, distance of the placement of the end 1707 of the CVC 1705 (e.g., indicated by marker 1734) relative to the desired location 1737 and/or anatomical location 1709 (e.g., indicated by marker 1736), and the acceptability of the placement of the tip 1707. This computed distance may be tracked between different x-rays to assess CVC position changes over time between x-rays. In FIG. 8, as depicted, the indication 1754 indicates that the tip 1707 is detected and in a proper position. In addition, the indication 1754 also lists the typical potential complications associated with the placement of the device present in the image 1702, e.g., a CVC, within the anatomical region, e.g., a chest, represented within the image 1702, and provides an automated assessment of each of the conditions. In particular in FIG. 8, none of the listed complications is detected to be present by the AI system 120/220.

With regard to FIG. 9, the indications 1754 provide information regarding the results of the analysis of the image 1702 by the AI system 120/220 that illustrate that the end of the tube or line is not properly positioned relative to the desired location and/or reference or anatomical location 1709 and that a complication in the form of a hydrothorax is detected and located in the right lung. In certain embodiments, the indication(s) 1754 may state the tube or line 1705 is placed properly, misplaced, provide an indication of what is wrong with the location, or provide instructions for correcting a location.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Thus, certain examples facilitate image acquisition and analysis at the point of care such as via a portable imaging device at the point of patient imaging. If images should be re-taken, further analysis done right away, and/or other criticality explored sooner, rather than later, the example systems, apparatus, and methods disclosed and described herein can facilitate such action to automate analysis, streamline workflow, and improve patient care.

Certain examples provide a specially-configured imaging apparatus that can acquire images and operate as a decision support tool at the point of care for a critical care team. Certain examples provide an imaging apparatus that functions as a medical device to provide and/or facilitate diagnosis at the point of care to detect radiological findings, etc. The apparatus can trigger a critical alert for a radiologist and/or critical care team to bring immediate attention to the patient. The apparatus enables patient triaging after the patient's exam, such as in a screening environment, wherein negative tests allow the patient to return home, while a positive test would require the patient to be seen by a physician before returning home.

In certain examples, a mobile device and/or cloud product enables a vendor-neutral solution, proving point of care alerts on any digital x-ray system (e.g., fully integrated, upgrade kit, etc.). In certain examples, embedded AI algorithms executing on a mobile imaging system, such as a mobile x-ray machine, etc., provide point of care alerts during and/or in real-time following image acquisition, etc.

By hosting AI on the imaging device, the mobile x-ray system can be used in rural regions without hospital information technology networks, or even on a mobile truck that brings imaging to patient communities, for example. Additionally, if there is long latency to send an image to a server or cloud, AI on the imaging device can instead be executed and generate output back to the imaging device for further action. Rather than having the x-ray technologist moved onto the next patient and the x-ray device no longer at the patient's bedside with the clinical care team, image processing, analysis, and output can occur in real time (or substantially real time given some data transfer/retrieval, processing, and output latency) to provide a relevant notification to the clinical care team while they and the equipment are still with or near the patient. For trauma cases, for example, treatment decisions need to be made fast, and certain examples alleviate the delay found with other clinical decision support tools.

Mobile X-ray systems travel throughout the hospital to the patient bedside (e.g., emergency room, operating room, intensive care unit, etc. Within a hospital, network communication may be unreliable in "dead" zones of the hospital (e.g., basement, rooms with electrical signal interference or blockage, etc.). If the X-ray device relies on building Wi-Fi, for example, to push the image to a server or cloud which is hosting the AI model and then wait to receive the AI output back to the X-ray device, then patient is at risk of not having reliability in critical alerts when needed. Further, if a network or power outage impacts communications, the AI operating on the imaging device can continue to function as a self-contained, mobile processing unit.

Examples of alerts generated for general radiology can include critical alerts (e.g., for mobile x-ray, etc.) such as tubes and line placement, pleural effusion, lobar collapse, retained CVC guidewire, pneumoperitoneum, pneumomediastinum, pneumonia, etc.; screening alerts (e.g., for fixed x-ray, etc.) such as tuberculosis, lung nodules, etc.; quality alerts (e.g., for mobile and/or fixed x-ray, etc.) such as patient positioning, clipped anatomy, inadequate technique, image artifacts, etc.

Thus, certain examples improve accuracy of an artificial intelligence algorithm Certain examples factor in patient medical information as well as image data to more accurately predict presence of a critical finding, an urgent finding, and/or other issue.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

Technical effects of the disclosed subject matter include providing systems and methods that utilize AI (e.g., deep learning networks) to determine whether or not a medically placed tube or line is properly placed within a region of interest (e.g., relative to an anatomical reference landmark). The systems and methods may provide feedback in real time that in a more accurate and quicker manner determine if a medically placed tube or line is misplaced. Thus, enabling fast intervention, if needed, to move the tube or line to the appropriate location for patient safety.

This written description uses examples to disclose the subject matter, including the best mode, and also to enable any person skilled in the art to practice the subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A medical image processing system, comprising:

a. a display;

b. a processor; and c. a memory storing processor-executable code that when executed by the processor causes:

i. receiving an image of a region of interest of a patient with a medical tube or line disposed within the region of interest;

ii. detecting the medical tube or line within the image;

iii. detecting one or more reference landmarks within the region of interest within the image, wherein the one or more reference landmarks are internal to the patient;

iv. generating a patient coordinate system for the image utilizing the one or more reference landmarks;

v. generating a combined image by superimposing a first graphical marker on the image that indicates a location of an end of the medical tube or line, and a second graphical marker on the image that indicates a position of the one or more reference landmarks, vi. generating an indication in the combined image of a position of the end of the medical tube relative to the one or more reference landmarks using the patient coordinate system; and vii. presenting the combined image on the display.

2. The medical image processing system of claim 1, wherein to generate the patient coordinate system, the processor-executable code when executed by the processor causes:

a. determining a vertical axis of the patient coordinate system within the image; and b. determining a horizontal axis of the patient coordinate system within the image.

3. The medical image processing system of claim 2, wherein to determine the vertical axis of the patient coordinate system, the processor-executable code when executed by the processor causes:

a. detecting one or more first anatomical markers present in the image; and b. determining the vertical axis for the patient coordinate system relative to the one or more first anatomical markers.

4. The medical image processing system of claim 3, wherein to generate the patient coordinate system the processor-executable code when executed by the processor causes:

a. detecting one or more vertebrae as the one or more first anatomical markers within the image;

b. determining the vertical axis of the patient coordinate system using the one or more vertebrae.

5. The medical image processing system of claim 2, wherein to determine the horizontal axis of the patient coordinate system the processor-executable code when executed by the processor causes:

a. detecting one or more second anatomical markers present in the image; and b. determining the horizontal axis relative to the one or more second anatomical markers.

6. The medical image processing system of claim 5, wherein to detect one or more second anatomical markers present in the image, the processor-executable code when executed by the processor causes:

a. detecting one of a carina or trachea as the one or more second anatomical markers within the image;

b. determining the horizontal axis of the patient coordinate system using the carina or trachea.

7. The image processing system of claim 2, wherein to generate the indication in the combined image of a position of the end of the medical tube or line relative to the reference landmark using the patient coordinate system, the processor-executable code when executed by the processor causes:

a. generating an indication of a vertical distance between the first graphical marker and the second graphical marker along the vertical axis in the combined image; and b. generating an indication of a horizontal distance between the first graphical marker and the second graphical marker along the horizontal axis in the combined image.

8. The image processing system of claim 2, wherein to generate the indication in the combined image of a position of the end of the medical tube or line relative to the reference landmark using the patient coordinate system, the processor-executable code when executed by the processor causes generating a third graphical marker in the combined image representing the vertical axis and the horizontal axis of the patient coordinate system in the combined image.

9. The image processing system of claim 1, wherein to superimpose the first graphical marker on the image indicates a location an end of the medical tube or line, the processor-executable code when executed by the processor causes generating the first graphical marker to illustrate a position of an entire length of the medical tube or line including the end of the medical tube or line in the combined image.

10. The medical image processing system of claim 1, wherein to generate the patient coordinate system, the processor-executable code when executed by the processor causes generation of measuring units associated with the patient coordinate system, wherein the measuring units are selected from absolute measuring units and patient-specific measuring units.

11. The medical image processing system of claim 1, wherein the processor-executable code is an artificial intelligence.

12. The medical image processing system of claim 11, wherein the artificial intelligence when executed by the processor causes a determination of the placement of the end of the medical tube or line in the image relative to a threshold for proper placement of the end of the medical tube or line.

13. The medical image processing system of claim 11, wherein the medical tube or line is a central venous catheter.

14. An imaging system comprising:

a. a radiation source;

b. a detector alignable with the radiation source;

c. a display for presenting information to a user; and d. a controller connected to the display and operable to control the operation of the radiation source and detector to generate image data, the controller including an image processing system comprising:

a. a processor; and b. a memory storing processor-executable code that when executed by the processor causes:

i. receiving an image of a region of interest of a patient with a medical catheter, tube or line disposed within the region of interest;

ii. detecting the medical catheter, tube or line within the image;

iii. detecting at least one reference landmark within the region of interest within the image, wherein the at least one reference landmark is internal to the patient;

iv. generating a patient coordinate system relative to an anatomy of the patient within the image utilizing the at least one reference landmark;

v. a combined image by superimposing a first graphical marker on the image that indicates an end of the medical catheter, tube or line, a second graphical marker on the image that indicates the ate least one reference landmark, and a third graphical marker the indicates the patient coordinate system; and vi. displaying the combined image on the display.

15. The imaging system of claim 14, wherein to generate the patient coordinate system, the processor-executable code when executed by the processor causes:

a. determining a vertical axis of the patient coordinate system within the image; and b. determining a horizontal axis of the patient coordinate system within the image.

16. The imaging system of claim 14, wherein to generate the indication in the combined image of a position of the end of the medical tube or line relative to the reference landmark using the patient coordinate system, the processor-executable code when executed by the processor causes:

a. generating an indication of a vertical distance between the first graphical marker and the second graphical marker along the vertical axis in the combined image; and b. generating an indication of a horizontal distance between the first graphical marker and the second graphical marker along the horizontal axis in the combined image.

17. The imaging system of claim 14, wherein to generate the indication in the combined image of a position of the end of the medical tube or line relative to the reference landmark using the patient coordinate system, the processor-executable code when executed by the processor causes generating a third graphical marker in the combined image representing the vertical axis and the horizontal axis of the in the combined image.

18. A method for medical image processing, comprising:

a. receiving, via a processor, an image of a region of interest of a patient with a medical catheter, tube or line disposed within the region of interest;

b. detecting, via the processor, the medical catheter, tube or line within the image;

c. detecting, via the processor, a number of reference landmarks within the region of interest within the image, wherein the number of reference landmarks are each internal to the patient;

d. generating, via the processor, a patient coordinate system employing the detected number of reference landmarks;

e. generating, via the processor, a combined image by superimposing a first graphical marker on the image that indicates an end of the medical catheter, tube or line, and a second graphical marker on the image that indicates the reference landmark; and f. causing, via the processor, display of the combined image on a display.

19. The method of claim 18, wherein the step of generating, via the processor, a combined image further comprises superimposing a third graphical marker in the combined image representing the vertical axis and the horizontal axis of the patient coordinate system in the combined image.

20. The method of claim 18, wherein the step of generating, via the processor, a combined image further comprises:

a. generating an indication of a vertical distance between the first graphical marker and the second graphical marker along the vertical axis in the combined image; and b. generating an indication of a horizontal distance between the first graphical marker and the second graphical marker along the horizontal axis in the combined image.

* * * * *